United States Patent [19]
Masiakowski

[11] Patent Number: 6,060,276
[45] Date of Patent: May 9, 2000

[54] NUCLEIC ACIDS ENCODING NOVEL ORPHAN CYTOKINE RECEPTORS

[75] Inventor: Piotr J. Masiakowski, Pleasant Valley, N.Y.

[73] Assignee: Regeneron Pharmaceuticals, Inc., Tarrytown, N.Y.

[21] Appl. No.: 09/012,072

[22] Filed: Jan. 22, 1998

[51] Int. Cl.[7] .......................... C12N 15/12; C07K 14/705

[52] U.S. Cl. .................... 435/69.1; 536/23.5; 435/252.3; 435/254.2; 435/320.1; 435/325; 435/348

[58] Field of Search ........................... 536/23.5; 435/69.1, 435/320.1, 252.3, 254.11, 325, 348, 254.2

[56] References Cited

PUBLICATIONS

Vigon et al., Proc. Natl. Acad. Sci., 89, 5640–5644, Jun. 1992.
Sambrook et al., Molecular Cloning, A Laboratory Manual, Vol. 3, 16.20–16.30 and 17.3–17.28, 1989.

*Primary Examiner*—Sally P. Teng
*Attorney, Agent, or Firm*—Robert J. Cobert

[57] ABSTRACT

The present invention provides for nucleic acid sequences that encode novel mammalian receptor polypeptides, designated OCR1. The invention also provides assay systems that may be used to detect and/or measure ligands that bind the MAMMALIAN OCR1 gene product. The present invention also provides for diagnostic and therapeutic methods based on the interaction between MAMMALIAN OCR1 and agents that initiate signal transduction through binding to MAMMALIAN OCR1. In a specific embodiment, the MAMMALIAN OCR1 may HUMAN OCR1 or MOUSE OCR1.

6 Claims, No Drawings

NUCLEIC ACIDS ENCODING NOVEL ORPHAN CYTOKINE RECEPTORS

Throughout this application various publications are referenced. The disclosures of these publications in their entireties are hereby incorporated by reference into this application.

INTRODUCTION

The field of this invention is polypeptide molecules which regulate cell function, nucleic acid sequences encoding the polypeptides, and methods of using the nucleic acid sequences and the polypeptides. The present invention provides for novel receptor molecules, their use and assay systems useful for identifying novel ligands that interact with these receptors.

BACKGROUND OF THE INVENTION

The ability of ligands to bind cells and thereby elicit a phenotypic response such as development, differentiation, growth, proliferation, survival and regeneration in such cells is often mediated through transmembrane receptors. The extracellular portion of each receptor is generally the most distinctive portion of the molecule, as it provides the protein with its ligand-recognizing characteristic. In the case of receptor tyrosine kinases (RTKs), binding of a ligand to the extracellular domain results in signal transduction via an intracellular tyrosine kinase catalytic domain which transmits a biological signal to intracellular target proteins. The particular array of sequence motifs of this intracellular tyrosine kinase catalytic domain determines its access to potential kinase substrates (Mohammadi, et al., 1990, Mol. Cell. Biol. 11: 5068–5078; Fantl, et al., 1992, Cell 69:413–413). For instance, growth hormone (GH) and prolactin (PRL) receptor signal transduction is mediated by a signaling system that links activation of the GH or PRL receptor at the cell surface to changes in gene transcription in the nucleus. This pathway utilizes the Jak/Stat (Janus kinase/signal transducer and activator of transcription) pathway used by many growth factors and cytokines (See Watson, et al., 1996, Rev. Reprod. 1:1–5).

The tissue distribution of a particular receptor within higher organisms provides relevant data as to the biological function of the receptor. The RTKs for some growth and differentiation factors, such as fibroblast growth factor (FGF), are widely expressed and therefore appear to play some general role in tissue growth and maintenance. Members of the Trk RTK family (Glass & Yancopoulos, 1993, Trends in Cell Biol. 3:262–268) of receptors are more generally limited to cells of the nervous system, and the neurotrophins which bind these receptors promote the differentiation of diverse groups of neurons in the brain and periphery (Lindsay, R. M, 1993, in Neurotrophic Factors, S. E. Loughlin & J. H. Fallon, eds., pp. 257–284 (San Diego, Calif., Academic Press).

Prolactin (PRL), an anterior pituitary hormone, is encoded by a member of the growth hormone/prolactin/placental lactogen gene family. In mammals, it is primarily responsible for the development of the mammary gland and lactation. In addition to its classical effects in the mammary gland, PRL has been shown to have a number of other actions, all of which are initiated by an interaction with transmembrane receptors located on the cell surface and widely distributed in a number of tissues. Studies have shown that PRL receptor expression levels are differentially regulated in different tissues (Zhuang and Dufau, 1996, J. Biol. Chem. 271:10242–10246; Moldrup, et al., 1996, Mol. Endocrinol. 10:661–671; Borg, et al., 1996, Eur J. Endocrinol. 134:751–757). For example, in rat liver, a tissue with a relatively high level of PRL binding, receptor levels vary during the different phases of the estrous cycle, increase during pregnancy, and are markedly stimulated by estrogens. Furthermore, PRL plays a major role in the regulation of expression of the PRL receptor, inducing both up- and down-regulation depending on PRL concentration and duration of exposure (See, for example, Di Carlo, et al., 1995, Endocrinology 136:4713–4716; Matsuda and Mori, 1996, Zoolog. Sci. 13:435–441; Matsuda and Mori, 1997, Zoolog. Sci. 14:159–165).

The cellular environment in which a receptor is expressed may influence the biological response exhibited upon binding of a ligand to the receptor. Thus, for example, when a neuronal cell expressing a Trk receptor is exposed to a neurotrophin which binds that receptor, neuronal survival and differentiation results. When the same receptor is expressed by a fibroblast, exposure to the neurotrophin results in proliferation of the fibroblast (Glass, et al., 1991, Cell 66:405–413). Thus, it appears that the extracellular domain provides the determining factor as to the ligand specificity, and once signal transduction is initiated the cellular environment will determine the phenotypic outcome of that signal transduction.

Comparison of the rat PRL receptor sequence with that of the mammalian GH receptor sequence has demonstrated some regions of identity between the two receptors, suggesting that the receptors originate from a common ancestry and may actually belong to a larger family of receptors, all of which share certain sequence homologies and perhaps related biological function. Because ligands and their receptors appear to mediate a number of important biological functions during development (e.g., bone growth, sexual maturation) as well as in the adult (e.g., homeostasis, reproduction), the identification and isolation of novel receptors may be used as a means of identifying new ligands or to study intracellular signalling pathways that may play a crucial role during development and in the maintenance of the adult phenotype. Often such novel receptors are identified and isolated by searching for additional members of known families of receptors using, for example, PCR-based screens involving known regions of homology among receptor family members. (See, for example, Maisonpierre, et al., 1993, Oncogene 8:1631–1637). Isolation of such so called "orphan" receptors, for which no ligand is known, and subsequent determination of the tissues in which such receptors are expressed, provides insight into the regulation of the development, differentiation, growth, proliferation, survival and regeneration of cells in target tissues. Further, such receptors may be used to isolate their cognate ligand, which may then be used to regulate the development, differentiation, growth, proliferation, survival and regeneration of cells expressing the receptor.

SUMMARY OF THE INVENTION

The present invention provides for a novel mammalian receptor, termed orphan cytokine receptor-1 (OCR1), which is expressed at high levels in heart, brain, placenta, skeletal muscle, and pancreas, and at moderate levels in lung, prostate, testis, uterus, small intestine and colon. Specifically, the present invention provides for a novel human receptor termed HUMAN OCR1. The present invention further provides for a novel mouse receptor termed MOUSE OCR1. Throughout this description, reference to MAMMALIAN OCR1 includes, but is not limited to, the specific embodiments of HUMAN OCR1 and MOUSE OCR1 as described herein. The protein appears to be related to the cytokine family of receptors which includes, but is not limited to, the prolactin/growth hormone receptors. The present invention further provides for an isolated nucleic acid molecule encoding MAMMALIAN OCR1.

The present invention also provides for a protein or polypeptide that comprises the extracellular domain of MAMMALIAN OCR1 and the nucleic acid which encodes such extracellular domain.

The invention further provides for vectors comprising an isolated nucleic acid molecule encoding MAMMALIAN OCR1 or its extracellular domain, which can be used to express MAMMALIAN OCR1 in bacteria, yeast, insect or mammalian cells.

The present invention further provides for use of the MAMMALIAN OCR1 receptor or its extracellular or intracellular domain in screening for drugs that interact with MAMMALIAN OCR1. Novel agents that bind to the receptor(s) described herein may mediate survival and differentiation in cells naturally expressing the receptor, but also may confer survival and proliferation when used to treat cells engineered to express the receptor. In particular embodiments, the extracellular domain (soluble receptor) of MAMMALIAN OCR1 is utilized in screens for cognate ligands.

The invention also provides for a nucleic acid probe capable of hybridizing with a sequence included within the nucleic acid sequence encoding MAMMALIAN OCR1 useful for the detection of MAMMALIAN OCR1 expressing tissue in humans and animals.

The invention further provides for antibodies directed against MAMMALIAN OCR1.

The present invention also has diagnostic and therapeutic utilities. In particular embodiments of the invention, methods of detecting aberrancies in the function or expression of the receptor described herein may be used in the diagnosis of endocrine or other disorders. In other embodiments, manipulation of the receptor or agonists which bind this receptor may be used in the treatment of, for example, endocrine disorders. In further embodiments, the extracellular domain of the receptor is utilized as a blocking agent which blocks the binding of ligand to target cells.

In a further embodiment of the invention, patients that suffer from an excess of HUMAN OCR1 may be treated by administering an effective amount of anti-sense RNA or anti-sense oligodeoxyribonucleotides corresponding to the HUMAN OCR1 gene coding region, thereby decreasing expression of HUMAN OCR1.

DETAILED DESCRIPTION OF THE INVENTION

The invention provides MAMMALIAN OCR1 polypeptides which include isolated MAMMALIAN OCR1 polypeptides and recombinant polypeptides comprising a MAMMALIAN OCR1 amino acid sequence, or a functional MAMMALIAN OCR1 polypeptide domain thereof having an assay-discernable MAMMALIAN OCR1-specific activity. Accordingly, the polypeptides may be deletion mutants of the disclosed MAMMALIAN OCR1 polypeptide and may be provided as fusion products, e.g., with non-MAMMALIAN OCR1 polypeptides. The subject MAMMALIAN OCR1 polypeptides have MAMMALIAN OCR1-specific activity or function.

A number of applications for MAMMALIAN OCR1 polypeptides are suggested from their properties. MAMMALIAN OCR1 polypeptides may be useful in the study and treatment of conditions similar to those which are treated using cytokines and/or hormones. Furthermore, the MAMMALIAN OCR1 cDNA may be useful as a diagnostic tool, such as through the use of oligonucleotides as primers in a PCR test to amplify those sequences having similarities to the oligonucleotide primer, and to see how much MAMMALIAN OCR1 mRNA is present in a particular tissue or sample. The isolation of MAMMALIAN OCR1, of course, also provides the key to isolate its putative ligand, other MAMMALIAN OCR1 binding polypeptides, and/or study its properties.

MAMMALIAN OCR1-specific activity or function may be determined by convenient in vitro, cell based or in vivo assays. In vitro or cell based assays include but are not limited to binding assays and cell culture assays. In vivo assays include but are not limited to immune response, gene therapy and transgenic animals. Binding assays encompass any assay where the specific molecular interaction of a MAMMALIAN OCR1 polypeptide with a binding target is evaluated. The binding target may be a natural binding target, or a nonnatural binding target such as a specific immune polypeptide such as an antibody, or a MAMMALIAN OCR1-specific binding agent.

The claimed MAMMALIAN OCR1 polypeptides may be isolated or pure—an "isolated" polypeptide is one that is no longer accompanied by some of the material with which it is associated in its natural state, and that preferably constitutes at least about 0.5%, and more preferably at least about 5% by weight of the total polypeptide in a given sample; a "pure" polypeptide constitutes at least about 90%, and preferably at least about 99% by weight of the total polypeptide in a given sample. The subject polypeptides may be synthesized, produced by recombinant technology, or purified from cells. A wide variety of molecular and biochemical methods are available for biochemical synthesis, molecular expression and purification of the subject compositions, see e.g., Molecular Cloning, A Laboratory Manual (Sambrook, et al., Cold Spring Harbor Laboratory, Cold Spring Harbor, N.Y.), Current Protocols in Molecular Biology (Eds. Ausubel, et al., Greene Publ. Assoc., Wiley-Interscience, N.Y.).

The subject polypeptides find a wide variety of uses including but not limited to use as immunogens, targets in screening assays, bioactive reagents for modulating cell growth, differentiation and/or function. For example, the invention provides methods for modifying the physiology of a cell comprising contacting the extracellular surface of the cell or medium surrounding the cell with an exogenous MAMMALIAN OCR1 polypeptide under conditions whereby the added polypeptide specifically interacts with a component of the medium and/or the extracellular surface to effect a change in the physiology of the cell. According to these methods, the extracellular surface includes plasma membrane-associated molecules. The term "exogenous MAMMALIAN OCR1 polypeptide" refers to polypeptides not made by the cell or, if so, expressed at non-natural levels, times or physiologic locales. Media, include, but are not limited to, in vitro culture media and/or physiological fluids such as blood, synovial fluid and lymph. The polypeptides may be introduced, expressed, or repressed in specific populations of cells by any convenient way, including but not limited to, microinjection, promoter-specific expression of recombinant protein or targeted delivery of lipid vesicles.

The invention provides MAMMALIAN OCR1-specific binding agents, methods of identifying and making such agents, and their use in diagnosis, therapy and pharmaceutical development. MAMMALIAN OCR1-specific binding agents include MAMMALIAN OCR1-specific antibodies (See, e.g., Harlow and Lane (1988) Antibodies, A Laboratory Manual, Cold Spring Harbor Laboratory, Cold Spring Harbor, N.Y.) and also includes other binding agents identified with assays such as one-, two- and three-hybrid screens, and non-natural binding agents identified in screens of chemical libraries such as described below. Agents of particular interest modulate MAMMALIAN OCR1 polypeptide function.

The invention further provides for the production of secreted polypeptides consisting of the entire extracellular domain of MAMMALIAN OCR-1 fused to the human immunoglobulin gamma-1 constant region (IgG1 constant) or the human immunoglobulin gamma-1 Fc region (IgG1 Fc). This fusion polypeptide is called a MAMMALIAN OCR1 "receptorbody" (RB), and would be normally expected to exist as a dimer in solution based on formation of disulfide linkages between individual IgG1 constant region or IgG1 Fc region tails. MAMMALIAN OCR1 RB encoding nucleic acids may be part of expression vectors and may be incorporated into recombinant host cells, e.g., for expression and screening, for transgenic animals, or for functional studies such as the efficacy of candidate drugs for diseases associated with MAMMALIAN OCR1 polypeptide-mediated signal transduction. Expression systems are selected and/or tailored to effect MAMMALIAN OCR1 RB polypeptide structural and functional variants through alternative post-translational processing.

The invention provides MAMMALIAN OCR1 nucleic acids, which find a wide variety of applications, including but not limited to, use as translatable transcripts, hybridization probes, PCR primers, or diagnostic nucleic acids, as well as use in detecting the presence of MAMMALIAN OCR1 genes and gene transcripts and in detecting or amplifying nucleic acids encoding additional MAMMALIAN OCR1 homologs and structural analogs.

The subject nucleic acids are of synthetic/non-natural sequences and/or are isolated, i.e., no longer accompanied by some of the material with which it is associated in its natural state, preferably constituting at least about 0.5%, more preferably at least about 5% by weight of total nucleic acid present in a given fraction, and usually recombinant, meaning they comprise a non-natural sequence or a natural sequence joined to a nucleotide(s) other than that to which it is joined on a natural chromosome. Nucleic acids comprising the nucleotide sequence disclosed herein and fragments thereof, contain such sequence or fragment at a terminus, immediately flanked by a sequence other than that to which it is joined on a natural chromosome, or flanked by a native flanking region fewer than 10 kb, preferably fewer than 2 kb, which is immediately flanked by a sequence other than that to which it is joined on a natural chromosome. While the nucleic acids are usually RNA or DNA, it is often advantageous to use nucleic acids comprising other bases or nucleotide analogs to provide, example, modified stability.

The sequence of the disclosed MAMMALIAN OCR1 nucleic acid is used to obtain the deduced MAMMALIAN OCR1 polypeptide sequence. Further, the sequence of the disclosed MAMMALIAN OCR1 nucleic acid is optimized for selected expression systems (Holler, et al., (1993) Gene 136:323–328; Martin, et al., (1995) Gene 154:150–166) or used to generate degenerate oligonucleotide primers and probes for use in the isolation of natural MAMMALIAN OCR1 encoding nucleic acid sequences ("GCG" software, Genetics Computer Group, Inc., Madison, Wis.). MAMMALIAN OCR1 encoding nucleic acids may be part of expression vectors and may be incorporated into recombinant host cells, e.g., for expression and screening, for transgenic animals, or for functional studies such as the efficacy of candidate drugs for diseases associated with MAMMALIAN OCR1 polypeptide-mediated signal transduction. Expression systems are selected and/or tailored to effect MAMMALIAN OCR1 polypeptide structural and functional variants through alternative post-translational processing.

The invention also provides for nucleic acid hybridization probes and replication/amplification primers having a MAMMALIAN OCR1 cDNA-specific sequence and sufficient to effect specific hybridization with SEQ. ID. NO. 1 or SEQ. ID. NO. 3. Demonstrating specific hybridization generally requires stringent conditions, for example, hybridizing in a buffer comprising 30% formamide in 5×SSPE (0.18 M NaCl, 0.01 M NaPO$_4$, pH 7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. MAMMALIAN OCR1 cDNA homologs can also be distinguished from one another using alignment algorithms, such as BLASTX (Altschul, et al., (1990) Basic Local Alignment Search Tool, J. Mol. Biol. 215:403–410).

MAMMALIAN OCR1 hybridization probes find use in identifying wild-type and mutant alleles in clinical and laboratory samples. Mutant alleles are used to generate allele-specific oligonucleotide (ASO) probes for high-throughput clinical diagnoses. MAMMALIAN OCR1 nucleic acids are also used to modulate cellular expression or intracellular concentration or availability of active MAMMALIAN OCR1 polypeptides. MAMMALIAN OCR1 inhibitory nucleic acids are typically antisense-single stranded sequences comprising complements of the disclosed MAMMALIAN OCR1 coding sequences. Antisense modulation of the expression of a given MAMMALIAN OCR1 polypeptide may employ antisense nucleic acids operably linked to gene regulatory sequences. Cells are transfected with a vector comprising a MAMMALIAN OCR1 sequence with a promoter sequence oriented such that transcription of the gene yields an antisense transcript capable of binding to endogenous MAMMALIAN OCR1 encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given MAMMALIAN OCR1 polypeptide may be administered to the target cell, in or temporarily isolated from a host, at a concentration that results in a substantial reduction in expression of the targeted polypeptide. An enhancement in MAMMALIAN OCR1 expression is effected by introducing into the targeted cell type MAMMALIAN OCR1 nucleic acids which increase the functional expression of the corresponding gene products. Such nucleic acids may be MAMMALIAN OCR1 expression vectors, vectors which upregulate the functional expression of an endogenous allele, or replacement vectors for targeted correction of mutant alleles. Techniques for introducing the nucleic acids into viable cells are known in the art and include, but are not limited to, retroviral-based transfection or viral coat protein-liposome mediated transfection.

The invention provides efficient methods of identifying agents, compounds or lead compounds for agents active at the level of MAMMALIAN OCR1 modulatable cellular function. Generally, these screening methods involve assaying for compounds which modulate the interaction of MAMMALIAN OCR1 with a natural MAMMALIAN OCR1 binding target. A wide variety of assays for binding agents are provided including, but not limited to, protein-protein binding assays, immunoassays, or cell based assays. Preferred methods are amenable to automated, cost-effective, high throughput screening of chemical libraries for lead compounds.

In vitro binding assays employ a mixture of components including a MAMMALIAN OCR1 polypeptide, which may be part of a fusion product with another peptide or polypeptide, e.g., a tag for detection or anchoring. The assay mixtures comprise a natural MAMMALIAN OCR1 binding target. While native binding targets may be used, it is frequently preferred to use portions thereof as long as the portion provides binding affinity and avidity to the subject MAMMALIAN OCR1 conveniently measurable in the assay. The assay mixture also comprises a candidate pharmacological agent. Candidate agents encompass numerous chemical classes, though typically they are organic compounds, preferably small organic compounds, and are obtained from a wide variety of sources including libraries of synthetic or natural compounds. A variety of other reagents such as salts, buffers, neutral proteins, e.g., albumin, detergents, protease inhibitors, nuclease inhibitors, or antimicrobial agents may also be included. The mixture components can be added in any order that provides for the requisite bindings and incubations may be performed at any temperature which facilitates optimal binding. The mixture is incubated under conditions whereby, but for the presence of the candidate pharmacological agent, the MAMMALIAN OCR1 polypeptide specifically binds the binding target, portion or analog with a reference binding affinity. Incubation periods are chosen for optimal binding but are also minimized to facilitate rapid, high throughput screening.

After incubation, the agent-biased binding between the MAMMALIAN OCR1 polypeptide and one or more binding targets is detected by any convenient way. For cell-free binding type assays, a separation step is often used to separate bound from unbound components. Separation may be effected by any number of methods that include, but are not limited to, precipitation or immobilization followed by washing by, e.g., membrane filtration or gel chromatography. For cell-free binding assays, one of the components usually comprises or is coupled to a label. The label may provide for direct detection as radioactivity, luminescence, optical or electron density, or indirect detection such as an epitope tag or an enzyme. A variety of methods may be used to detect the label depending on the nature of the label and other assay components, including but not limited to, through optical or electron density, radiative emissions, nonradiative energy transfers, or indirectly detected with, as a nonlimiting example, antibody conjugates. A difference in the binding affinity of the MAMMALIAN OCR1 polypeptide to the target in the absence of the agent as compared with the binding affinity in the presence of the agent indicates that the agent modulates the binding of the MAMMALIAN OCR1 polypeptide to the corresponding binding target. A difference, as used herein, is statistically significant and preferably represents at least a 50%, more preferably at least a 90% difference.

The invention provides for a method for modifying the physiology of a cell comprising an extracellular surface in contact with a medium, said method comprising the step of contacting said medium with an exogenous MAMMALIAN OCR1 polypeptide under conditions whereby said polypeptide specifically interacts with at least one of the components of said medium to effect a change in the physiology of said cell.

The invention further provides for a method for screening for biologically active agents, said method comprising the steps of a) incubating a MAMMALIAN OCR1 polypeptide in the presence of a MAMMALIAN OCR1 polypeptide-specific binding target and a candidate agent, under conditions whereby, but for the presence of said agent, said polypeptide specifically binds said binding target at a reference affinity; b) detecting the binding affinity of said polypeptide to said binding target to determine an agent-biased affinity, wherein a difference between the agent-biased affinity and the reference affinity indicates that said agent modulates the binding of said polypeptide to said binding target.

One embodiment of the invention is an isolated MAMMALIAN OCR1 polypeptide comprising the amino acid sequence as set forth herein or a fragment thereof having MAMMALIAN OCR1-specific activity.

Another embodiment of the invention is a recombinant nucleic acid encoding MAMMALIAN OCR1 polypeptide comprising the amino acid sequence as set forth herein or a fragment thereof having MAMMALIAN OCR1-specific activity.

Still another embodiment is an isolated nucleic acid comprising a nucleotide sequence as set forth herein in SEQ. ID NO. 3 or a fragment thereof having at least 18 consecutive bases and which can specifically hybridize with a nucleic acid having the sequence of native MAMMALIAN OCR1.

The present invention also provides for antibodies to the MAMMALIAN OCR1 polypeptides described herein which are useful for detection of the polypeptides in, for example, diagnostic applications. For preparation of monoclonal antibodies directed toward MAMMALIAN OCR1 polypeptides, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy", Alan R. Liss, Inc. pp. 77–96) and the like are within the scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to the MAMMALIAN OCR1 polypeptides described herein. For the production of antibody, various host animals can be immunized by injection with the MAMMALIAN OCR1 polypeptides, or fragments or derivatives thereof, including but not limited to rabbits, mice and rats. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected MAMMALIAN OCR1 polypeptide epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include, but are not limited to, the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques including, but not limited to, immunoabsorption or immunoaffinity chromatography, chromatographic methods such as HPLC (high performance liquid chromatography), or a combination thereof.

The following example is offered by way of illustration and not by way of limitation.

EXAMPLE 1

Cloning and Sequencing of Nucleic Acid Encoding Mouse OCR-1

Amino acid sequences of known human and mouse members of the cytokine receptor family were used as tblastn queries to search the NIH EST database of random fragments of mRNA sequences (Altschul et al., (1990), Basic local alignment search tool J. Mol. Biol. 215:403–10). Each query generated a list of hits, i.e. EST sequences with a substantial sequence similarity to the query sequence. Typically, the hits on top of the list corresponded to mRNA copies of the query protein, followed by ESTs derived from other members of the family and random-chance similarities.

A parser program was used to combine and sort all the hits from searches with all the members of the family. This allowed rapid subtraction of all the hits corresponding to known proteins. The remaining hits were analyzed for conservation of sequence motifs characteristic for the family. Additional database searches were performed to identify overlapping ESTs. Two cDNA clone(s) from the I.M.A.G.E. consortium were discerned to contain homologous sequence. Clone #387741 (the '741 clone) (GeneBank Accession No. W66776) and clone #479043 (the '043 clone) (GeneBank Accession No. AA049280) were obtained from Research Genetics, Inc. (Huntsville, AL) and sequenced using the ABI 373A DNA sequencer and Taq Dideoxy Terminator Cycle Sequencing Kit (Applied Biosystems, Inc., Foster City, Calif.).

The '043 clone contained a partial sequence of MOUSE OCR1 and clone '741 contained a 1215 bp nucleotide sequence (SEQ. ID NO. 1) that translated into a full length single coding frame encoding a 406 amino acid protein (SEQ. ID NO. 2) designated MOUSE OCR1 as set forth below. MOUSE OCR1 revealed sequence similarity to members of the cytokine receptor family.

```
                           10            20            30            40            50            60
                      *         *         *         *         *         *         *         *         *         *         *         *
SEQ. ID NO. 1: TCC TCG CTG TGG TCG CCT CTG TTG CTC TGT GTC CTC GGG GTG CCT CGG GGC GGA TCG GCA
SEQ. ID NO. 2: Ser Ser Leu Trp Ser Pro Leu Leu Leu Cys Val Leu Gly Val Pro Arg Gly Gly Ser Gly>

70            80            90           100           110           120
                      *         *         *         *         *         *         *         *         *         *         *         *
               GCC CAC ACA GCT GTA ATC AGC CCC CAG GAC CCC ACC CTT CTC ATC GGC TCC TCC CTG CAA
               Ala His Thr Ala Val Ile Ser Pro Gln Asp Pro Thr Leu Leu Ile Gly Ser Ser Leu Gln>

130           140           150           160           170           180
                      *         *         *         *         *         *         *         *         *         *         *         *
               GCT ACC TGC TCT ATA CAT GGA GAC ACA CCT GGG GCC ACC GCT GAG GCC CTC TAC TGG ACC
               Ala Thr Cys Ser Ile His Gly Asp Thr Pro Gly Ala Thr Ala Glu Gly Leu Tyr Trp Thr>

190           200           210           220           230           240
                      *         *         *         *         *         *         *         *         *         *         *         *
               CTC AAT GGT CGC CGC CTG CCC TCT GAG CTG TCC CGC CTC CTT AAC ACC TCC ACC CTG GCC
               Leu Asn Gly Arg Arg Leu Pro Ser Glu Leu Ser Arg Leu Leu Asn Thr Ser Thr Leu Ala>

250           260           270           280           290           300
                      *         *         *         *         *         *         *         *         *         *         *         *
               CTG GCC CTG GCT AAC CTT AAT GGG TCC AGG CAG CAG TCA GGA GAC AAT CTG GTG TGT CAC
               Leu Ala Leu Ala Asn Leu Asn Gly Ser Arg Gln Gln Ser Gly Asp Asn Leu Val Cys His>

310           320           330           340           350           360
                      *         *         *         *         *         *         *         *         *         *         *         *
               GCC CGA GAT GGC AGC ATT CTG GCT GGC TCC TGC CTC TAT GTT GGC TTG CCC CCT GAG AAG
               Ala Arg Asp Gly Ser Ile Leu Ala Gly Ser Cys Leu Tyr Val Gly Leu Pro Pro Glu Lys>

370           380           390           400           410           420
                      *         *         *         *         *         *         *         *         *         *         *         *
               CCT TTT AAC ATC AGC TGC TGG TCC CGG AAC ATG AAG GAT CTC ACG TGC CGC TGG ACA CCG
               Pro Phe Asn Ile Ser Cys Trp Ser Arg Asn Met Lys Asp Leu Thr Cys Arg Trp Thr Pro>
```

-continued

```
                    430         440         450         460         470         480
                     *           *           *           *           *           *
              GGT GCA CAC GGG GAG ACA TTC TTA CAT ACC AAC TAC TCC CTC AAG TAC AAG CTG AGG TGG
              Gly Ala His Gly Glu Thr Phe Leu His Thr Asn Tyr Ser Leu Lys Tyr Lys Leu Arg Trp>

490         500         510         520         530         540
                     *           *           *           *           *           *
              TAC GGT CAG GAT AAC ACA TGT GAG GAG TAC CAC ACT GTG GGC CCT CAC TCA TGC CAT ATC
              Tyr Gly Gln Asp Asn Thr Cys Glu Glu Tyr His Thr Val Gly Pro His Ser Cys His Ile>

550         560         570         580         590         600
                     *           *           *           *           *           *
              CCC AAG GAC CTG GCC CTC TTC ACT CCC TAT GAG ATC TGG GTG GAA GCC ACC AAT CGC CTA
              Pro Lys Asp Leu Ala Leu Phe Thr Pro Tyr Glu Ile Trp Val Glu Ala Thr Asn Arg Leu>

610         620         630         640         650         660
                     *           *           *           *           *           *
              GGC TCA GCA AGA TCT GAT GTC CTC ACA CTG GAT GTC CTG GAC GTG GTG ACC ACG GAC CCC
              Gly Ser Ala Arg Ser Asp Val Leu Thr Leu Asp Val Leu Asp Val Val Thr Thr Asp Pro>

670         680         690         700         710         720
                     *           *           *           *           *           *
SEQ. ID NO. 1: CCA CCC GAC GTG CAC GTG AGC CGC GTT GGG GGC CTC GAG GAC CAG CTG AGT GTG CGC TGG
SEQ. ID NO. 2: Pro Pro Asp Val His Val Ser Arg Val Gly Gly Leu Glu Asp Gln Leu Ser Val Arg Trp>

730         740         750         760         770         780
                     *           *           *           *           *           *
              GTC TCA CCA CCA GCT CTC AAG GAT TTC CTC TTC CAA GCC AAG TAC CAG ATC CGC TAC CGC
              Val Ser Pro Pro Ala Leu Lys Asp Phe Leu Phe Gln Ala Lys Tyr Gln Ile Arg Tyr Arg>

790         800         810         820         830         840
                     *           *           *           *           *           *
              GTG GAG GAC AGC GTG GAC TGG AAG GTG GTG GAT GAC GTC AGC AAC CAG ACC TCC TGC CGT
              Val Glu Asp Ser Val Asp Trp Lys Val Val Asp Asp Val Ser Asn Gln Thr Ser Cys Arg>

850         860         870         880         890         900
                     *           *           *           *           *           *
              CTC GCG GGC CTG AAG CCC GGC ACC GTT TAC TTC GTC CAA GTG CGT TGT AAC CCA TTC GGG
              Leu Ala Gly Leu Lys Pro Gly Thr Val Tyr Phe Val Gln Val Arg Cys Asn Pro Phe Gly>

910         920         930         940         950         960
                     *           *           *           *           *           *
              ATC TAT GGG TCG AAA AAG GCG GGA ATC TGG AGC GAG TGG AGC CAC CCC ACC GCT GCC TCC
              Ile Tyr Gly Ser Lys Lys Ala Gly Ile Trp Ser Glu Trp Ser His Pro Thr Ala Ala Ser>

970         980         990        1000        1010        1020
                     *           *           *           *           *           *
              ACC CCT CGA AGT GAG CGC CCG GGC CCG GGC GGC GGG GTG TGC GAG CCG CGG GGC GGC GAG
              Thr Pro Arg Ser Glu Arg Pro Gly Pro Gly Gly Gly Val Cys Glu Pro Arg Gly Gly Glu>

1030        1040        1050        1060        1070        1080
                     *           *           *           *           *           *
              CCC AGC TCG GGC CCG GTG CGG CGC GAG CTC AAG CAG TTC CTC GGC TGG CTC AAG AAG CAC
              Pro Ser Ser Gly Pro Val Arg Arg Glu Leu Lys Gln Phe Leu Gly Trp Leu Lys Lys His>

1090        1100        1110        1120        1130        1140
                     *           *           *           *           *           *
              GCA TAC TGC TCG AAC CTT AGT TTC CGC CTG TAC GAC CAG TGG CGT GCT TGG ATG CAG AAG
              Ala Tyr Cys Ser Asn Leu Ser Phe Arg Leu Tyr Asp Gln Trp Arg Ala Trp Met Gln Lys>

1150        1160        1170        1180        1190        1200
                     *           *           *           *           *           *
              TCA CAC AAG ACC CGA AAC CAG GAC GAG GGG ATC CTG CCC TCG GGC AGA CGG GGT GCG GCG
              Ser His Lys Thr Arg Asn Gln Asp Glu Gly Ile Leu Pro Ser Gly Arg Arg Gly Ala Ala>

1210
                     *
              AGA GGT CCT GCC GGC TAA
              Arg Gly Pro Ala Gly ***>
```

EXAMPLE 2

Cloning and Sequencing of Nucleic Acid Encoding Human OCR1

Amino acid sequences of known human and mouse members of the cytokine receptor family were used as tblastn queries to search the NIH EST database of random fragments of mRNA sequences (Altschul et al., (1990), Basic local alignment search tool J. Mol. Biol. 215:403–10). Each query generated a list of hits, i.e. EST sequences with a substantial sequence similarity to the query sequence. Typically, the hits on top of the list corresponded to mRNA copies of the query protein, followed by ESTs derived from other members of the family and random-chance similarities.

A parser program was used to combine and sort all the hits from searches with all the members of the family. This allowed rapid subtraction of all the hits corresponding to known proteins. The remaining hits were analyzed for conservation of sequence motifs characteristic for the family. Additional database searches were performed to identify overlapping ESTs. Three cDNA clones from the I.M.A.G.E. consortium were discerned to contain homologous sequence. Clone #324067 (the '067 clone) (GeneBank Accession No. W466040), clone #490004 (the '004 clone) (GeneBank Accession No. AA127694), and clone #302666 (the '666 clone) (GeneBank Accession No. W37175). All three were obtained from Genome Systems Inc. (St. Louis, Mo.) and sequenced using the ABI 373A DNA sequencer and Taq Dideoxy Terminator Cycle Sequencing Kit (Applied Biosystems, Inc., Foster City, Calif.).

Both the '004 clone and the '067 clone contained partial sequence and the '666 clone contained a 1302 bp nucleotide sequence (SEQ. ID NO. 3) that translated into a full length single coding frame encoding a 435 amino acid protein (SEQ. ID NO. 4) designated HUMAN OCR1 as set forth below. HUMAN OCR1 revealed sequence similarity to members of the cytokine receptor family.

```
                        10          20          30          40          50          60
                    *    *     *    *     *    *     *    *     *    *     *    *
SEQ. ID NO. 3: CGG CCG CCG CCG TTG CTG CCC CTG CTG CTG CTG CTC TGC GTC CTC GGG GCG CCG CGA GCC
SEQ. ID NO. 4: Arg Pro Pro Pro Leu Leu Pro Leu Leu Leu Leu Leu Cys Val Leu Gly Ala Pro Arg Ala>

70          80          90         100         110         120
                    *    *     *    *     *    *     *    *     *    *     *    *
               GGA TCA GGA GCC CAC ACA GCT GTG ATC AGT CCC CAG GAT CCC ACG CTT CTC ATC GGC TCC
               Gly Ser Gly Ala His Thr Ala Val Ile Ser Pro Gln Asp Pro Thr Leu Leu Ile Gly Ser>

130         140         150         160         170         180
                    *    *     *    *     *    *     *    *     *    *     *    *
               TCC CTG CTG GCC ACC TGC TCA GTG CAC GGA GAC CCA CCA GGA GCC ACC GCC GAG GGC CTC
               Ser Leu Leu Ala Thr Cys Ser Val His Gly Asp Pro Pro Gly Ala Thr Ala Glu Gly Leu>

190         200         210         220         230         240
                    *    *     *    *     *    *     *    *     *    *     *    *
               TAC TGG ACC CTC AAC GGG CGC CGC CTG CCC CCT GAG CTC TCC CGT GTA CTC AAC GCC TCC
               Tyr Trp Thr Leu Asn Gly Arg Arg Leu Pro Pro Glu Leu Ser Arg Val Leu Asn Ala Ser>

250         260         270         280         290         300
                    *    *     *    *     *    *     *    *     *    *     *
               ACC TTG GCT CTG GCC CTG GCC AAC CTC AAT GGG TCC AGG CAG CGG TCG GGG GAC AAC CTC
               Thr Leu Ala Leu Ala Leu Ala Asn Leu Asn Gly Ser Arg Gln Arg Ser Gly Asp Asn Leu>

310         320         330         340         350         360
                    *    *     *    *     *    *     *    *     *    *     *    *
               GTG TGC CAC GCC CGT GAC GGC AGC ATC CTG GCT GGC TCC TGC CTC TAT GTT GGC CTG CCC
               Val Cys His Ala Arg Asp Gly Ser Ile Leu Ala Gly Ser Cys Leu Tyr Val Gly Leu Pro>

370         380         390         400         410         420
                    *    *     *    *     *    *     *    *     *    *     *    *
               CCA GAG AAA CCC GTC AAC ATC AGC TGC TGG TCC AAG AAC ATG AAG GAC TTG ACC TGC CGC
               Pro Glu Lys Pro Val Asn Ile Ser Cys Trp Ser Lys Asn Met Lys Asp Leu Thr Cys Arg>

430         440         450         460         470         480
                    *    *     *    *     *    *     *    *     *    *     *    *
               TGG ACG CCA GGG GCC CAC GGG GAG ACC TTC CTC CAC ACC AAC TAC TCC CTC AAG TAC AAG
               Trp Thr Pro Gly Ala His Gly Glu Thr Phe Leu His Thr Asn Tyr Ser Leu Lys Tyr Lys>

490         500         510         520         530         540
                    *    *     *    *     *    *     *    *     *    *     *    *
               CTT AGG TGG TAT GGC CAG GAC AAC ACA TGT GAG GAG TAC CAC ACA GTG GGG CCC CAC TCC
               Leu Arg Trp Tyr Gly Gln Asp Asn Thr Cys Glu Glu Tyr His Thr Val Gly Pro His Ser>

550         560         570         580         590         600
                    *    *     *    *     *    *     *    *     *    *     *    *
               TGC CAC ATC CCC AAG GAC CTG GCT CTC TTT ACG CCC TAT GAG ATC TGG GTG GAG GCC ACC
               Cys His Ile Pro Lys Asp Leu Ala Leu Phe Thr Pro Tyr Glu Ile Trp Val Glu Ala Thr>

610         620         630         640         650         660
                    *    *     *    *     *    *     *    *     *    *     *    *
               AAC CGC CTG GGC TCT GCC CGC TCC GAT GTA CTC ACG CTG GAT ATC CTG GAT GTG GGG TCC
               Asn Arg Leu Gly Ser Ala Arg Ser Asp Val Leu Thr Leu Asp Ile Leu Asp Val Gly Ser>

670         680         690         700         710         720
                    *    *     *    *     *    *     *    *     *    *     *    *
SEQ. ID NO. 3: CAC CTG CCC CTC CCC AGC CCG GCA ACT CCC GGG TTG TCC CTG CTG GTC AGA GGG AAG GTA
SEQ. ID NO. 4: His Leu Pro Leu Pro Ser Pro Ala Thr Pro Gly Leu Ser Leu Leu Val Arg Gly Lys Val>
```

```
                730       740       750       760       770       780
                 *    *    *    *    *    *    *    *    *    *    *    *
            GTG ACC ACG GAC CCC CCG CCC GAC GTG CAC GTG AGC CGC GTC GGG GGC CTG GAG GAC CAG
            Val Thr Thr Asp Pro Pro Pro Asp Val His Val Ser Arg Val Gly Gly Leu Glu Asp Gln>

790       800       810       820       830       840
                      *    *    *    *    *    *    *    *    *    *    *    *
            CTG AGC GTG CGC TGG GTG TCG CCA CCC GCC CTC AAG GAT TTC CTC TTT CAA GCC AAA TAC
            Leu Ser Val Arg Trp Val Ser Pro Pro Ala Leu Lys Asp Phe Leu Phe Gln Ala Lys Tyr>

850       860       870       880       890       900
                           *    *    *    *    *    *    *    *    *    *    *    *
            CAG ATC CGC TAC CGA GTG GAG GAC AGT GTG GAC TGG AAG GTG GTG GAC GAT GTG AGC AAC
            Gln Ile Arg Tyr Arg Val Glu Asp Ser Val Asp Trp Lys Val Val Asp Asp Val Ser Asn>

910       920       930       940       950       960
                                *    *    *    *    *    *    *    *    *    *    *    *
            CAG ACC TCC TGC CGC CTG GCC GGC CTG AAA CCC GGC ACC GTG TAC TTC GTG CAA GTG CGC
            Gln Thr Ser Cys Arg Leu Ala Gly Leu Lys Pro Gly Thr Val Tyr Phe Val Gln Val Arg>

970       980       990      1000      1010      1020
                                     *    *    *    *    *    *    *    *    *    *    *    *
            TGC AAC CCC TTT GGC ATC TAT GGC TCC AAG AAA GCC GGG ATC TGG AGT GAG TGG AGC CAC
            Cys Asn Pro Phe Gly Ile Tyr Gly Ser Lys Lys Ala Gly Ile Trp Ser Glu Trp Ser His>

1030      1040      1050      1060      1070      1080
                                          *    *    *    *    *    *    *    *    *    *    *    *
            CCC ACA GCC GCC TCC ACT CCC CGC AGT GAG CGC CCG GGC CCG GGC GGC GGG GCG TGC GAA
            Pro Thr Ala Ala Ser Thr Pro Arg Ser Glu Arg Pro Gly Pro Gly Gly Gly Ala Cys Glu>

1090      1100      1110      1120      1130      1140
                                               *    *    *    *    *    *    *    *    *    *    *    *
            CCG CGG GGC GGA GAG CCG AGC TCG GGG CCG GTG CGG CGC GAG CTC AAG CAG TTC CTG GGC
            Pro Arg Gly Gly Glu Pro Ser Ser Gly Pro Val Arg Arg Glu Leu Lys Gln Phe Leu Gly>

1150      1160      1170      1180      1190      1200
                                                    *    *    *    *    *    *    *    *    *    *    *    *
            TGG CTC AAG AAG CAC GCG TAC TGC TCC AAC CTC AGC TTC CGC CTC TAC GAC CAG TGG CGA
            Trp Leu Lys Lys His Ala Tyr Cys Ser Asn Leu Ser Phe Arg Leu Tyr Asp Gln Trp Arg>

1210      1220      1230      1240      1250      1260
                                                         *    *    *    *    *    *    *    *    *    *    *    *
            GCC TGG ATG CAG AAG TCG CAC AAG ACC CGC AAC CAG CAC AGG ACG AGG GGA TCC TGC CCT
            Ala Trp Met Gln Lys Ser His Lys Thr Arg Asn Gln His Arg Thr Arg Gly Ser Cys Pro>

1270      1280      1290      1300
                                                              *    *    *    *    *    *    *    *    *
            CGG GCA GAC GGG GCA CGG CGA GAG GTC CTG CCA GAT AAG CTG TAG
            Arg Ala Asp Gly Ala Arg Arg Glu Val Leu Pro Asp Lys Leu ***>
```

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated nucleic acid molecule having a sequence selected from the group consisting of:

(a) the nucleotide sequence comprising the coding region of the HUMAN OCR1 as set forth in SEQ. ID. NO. 3; or (b) a nucleotide sequence which, as a result of the degeneracy of the genetic code differs from the nucleic acid of (a) and which encodes HUMAN OCR1.

2. A vector which comprises a nucleic acid molecule of claim 1.

3. A vector according to claim 2, wherein the nucleic acid molecule is operatively linked to an expression control sequence capable of directing its expression in a host cell.

4. A host-vector system for the production of HUMAN OCR1 polypeptide which comprises a vector of claim 3 in a host cell.

5. A host-vector system according to claim 4, wherein the host cell is a bacterial, yeast, insect or mammalian cell.

6. A method of producing HUMAN OCR1 polypeptide which comprises growing cells of a host-vector system of claim 5 under conditions permitting the production of HUMAN OCR1 polypeptide and recovering the HUMAN OCR1 polypeptide so produced.

* * * * *

SEQUENCE LISTING

```
<160> NUMBER OF SEQ ID NOS: 4

<210> SEQ ID NO 1
<211> LENGTH: 1218
<212> TYPE: DNA
<213> ORGANISM: MOUSE
<220> FEATURE:
<221> NAME/KEY: CDS
<222> LOCATION: (1)..(1215)
```

-continued

```
<400> SEQUENCE: 1 tcc tcg ctg tgg tcg cct ctg ttg ctc tgt gtc ctc ggg gtg cct cgg      48
Ser Ser Leu Trp Ser Pro Leu Leu Leu Cys Val Leu Gly Val Pro Arg
 1               5                  10                  15 ggc gga tcg gga gcc cac aca gct gta atc agc ccc cag gac ccc acc      96
Gly Gly Ser Gly Ala His Thr Ala Val Ile Ser Pro Gln Asp Pro Thr
             20                  25                  30 ctt ctc atc ggc tcc tcc ctg caa gct acc tgc tct ata cat gga gac     144
Leu Leu Ile Gly Ser Ser Leu Gln Ala Thr Cys Ser Ile His Gly Asp
         35                  40                  45 aca cct ggg gcc acc gct gag ggg ctc tac tgg acc ctc aat ggt cgc     192
Thr Pro Gly Ala Thr Ala Glu Gly Leu Tyr Trp Thr Leu Asn Gly Arg
     50                  55                  60 cgc ctg ccc tct gag ctg tcc cgc ctc ctt aac acc tcc acc ctg gcc     240
Arg Leu Pro Ser Glu Leu Ser Arg Leu Leu Asn Thr Ser Thr Leu Ala
 65                  70                  75                  80 ctg gcc ctg gct aac ctt aat ggg tcc agg cag cag tca gga gac aat     288
Leu Ala Leu Ala Asn Leu Asn Gly Ser Arg Gln Gln Ser Gly Asp Asn
                 85                  90                  95 ctg gtg tgt cac gcc cga gat ggc agc att ctg gct ggc tcc tgc ctc     336
Leu Val Cys His Ala Arg Asp Gly Ser Ile Leu Ala Gly Ser Cys Leu
            100                 105                 110 tat gtt ggc ttg ccc cct gag aag cct ttt aac atc agc tgc tgg tcc     384
Tyr Val Gly Leu Pro Pro Glu Lys Pro Phe Asn Ile Ser Cys Trp Ser
        115                 120                 125 cgg aac atg aag gat ctc acg tgc cgc tgg aca ccg ggt gca cac ggg     432
Arg Asn Met Lys Asp Leu Thr Cys Arg Trp Thr Pro Gly Ala His Gly
    130                 135                 140 gag aca ttc tta cat acc aac tac tcc ctc aag tac aag ctg agg tgg     480
Glu Thr Phe Leu His Thr Asn Tyr Ser Leu Lys Tyr Lys Leu Arg Trp
145                 150                 155                 160 tac ggt cag gat aac aca tgt gag gag tac cac act gtg ggc cct cac     528
Tyr Gly Gln Asp Asn Thr Cys Glu Glu Tyr His Thr Val Gly Pro His
                165                 170                 175 tca tgc cat atc ccc aag gac ctg gcc ctc ttc act ccc tat gag atc     576
Ser Cys His Ile Pro Lys Asp Leu Ala Leu Phe Thr Pro Tyr Glu Ile
            180                 185                 190 tgg gtg gaa gcc acc aat cgc cta ggc tca gca aga tct gat gtc ctc     624
Trp Val Glu Ala Thr Asn Arg Leu Gly Ser Ala Arg Ser Asp Val Leu
        195                 200                 205 aca ctg gat gtc ctg gac gtg gtg acc acg gac ccc cca ccc gac gtg     672
Thr Leu Asp Val Leu Asp Val Val Thr Thr Asp Pro Pro Pro Asp Val
    210                 215                 220 cac gtg agc cgc gtt ggg ggc ctg gag gac cag ctg agt gtg cgc tgg     720
His Val Ser Arg Val Gly Gly Leu Glu Asp Gln Leu Ser Val Arg Trp
225                 230                 235                 240 gtc tca cca cca gct ctc aag gat ttc ctc ttc caa gcc aag tac cag     768
Val Ser Pro Pro Ala Leu Lys Asp Phe Leu Phe Gln Ala Lys Tyr Gln
                245                 250                 255 atc cgc tac cgc gtg gag gac agc gtg gac tgg aag gtg gtg gat gac     816
Ile Arg Tyr Arg Val Glu Asp Ser Val Asp Trp Lys Val Val Asp Asp
            260                 265                 270 gtc agc aac cag acc tcc tgc cgt ctc gcg ggc ctg aag ccc ggc acc     864
Val Ser Asn Gln Thr Ser Cys Arg Leu Ala Gly Leu Lys Pro Gly Thr
        275                 280                 285 gtt tac ttc gtc caa gtg cgt tgt aac cca ttc ggg atc tat ggg tcg     912
Val Tyr Phe Val Gln Val Arg Cys Asn Pro Phe Gly Ile Tyr Gly Ser
    290                 295                 300
```

```
aaa aag gcg gga atc tgg agc gag tgg agc cac ccc acc gct gcc tcc      960
Lys Lys Ala Gly Ile Trp Ser Glu Trp Ser His Pro Thr Ala Ala Ser
305                 310                 315                 320 acc cct cga agt gag cgc ccg ggc ccg ggc ggc ggg gtg tgc gag ccg     1008
Thr Pro Arg Ser Glu Arg Pro Gly Pro Gly Gly Gly Val Cys Glu Pro
            325                 330                 335 cgg ggc ggc gag ccc agc tcg ggc ccg gtg cgg cgc gag ctc aag cag     1056
Arg Gly Gly Glu Pro Ser Ser Gly Pro Val Arg Arg Glu Leu Lys Gln
        340                 345                 350 ttc ctc ggc tgg ctc aag aag cac gca tac tgc tcg aac ctt agt ttc     1104
Phe Leu Gly Trp Leu Lys Lys His Ala Tyr Cys Ser Asn Leu Ser Phe
    355                 360                 365 cgc ctg tac gac cag tgg cgt gct tgg atg cag aag tca cac aag acc     1152
Arg Leu Tyr Asp Gln Trp Arg Ala Trp Met Gln Lys Ser His Lys Thr
370                 375                 380 cga aac cag gac gag ggg atc ctg ccc tcg ggc aga cgg ggt gcg gcg     1200
Arg Asn Gln Asp Glu Gly Ile Leu Pro Ser Gly Arg Arg Gly Ala Ala
385                 390                 395                 400 aga ggt cct gcc ggc taa                                             1218
Arg Gly Pro Ala Gly
            405

<210> SEQ ID NO 2
<211> LENGTH: 405
<212> TYPE: PRT
<213> ORGANISM: MOUSE

<400> SEQUENCE: 2

Ser Ser Leu Trp Ser Pro Leu Leu Cys Val Leu Gly Val Pro Arg
 1               5                  10                  15

Gly Gly Ser Gly Ala His Thr Ala Val Ile Ser Pro Gln Asp Pro Thr
                20                  25                  30

Leu Leu Ile Gly Ser Ser Leu Gln Ala Thr Cys Ser Ile His Gly Asp
            35                  40                  45

Thr Pro Gly Ala Thr Ala Glu Gly Leu Tyr Trp Thr Leu Asn Gly Arg
        50                  55                  60

Arg Leu Pro Ser Glu Leu Ser Arg Leu Leu Asn Thr Ser Thr Leu Ala
65                  70                  75                  80

Leu Ala Leu Ala Asn Leu Asn Gly Ser Arg Gln Gln Ser Gly Asp Asn
                85                  90                  95

Leu Val Cys His Ala Arg Asp Gly Ser Ile Leu Ala Gly Ser Cys Leu
            100                 105                 110

Tyr Val Gly Leu Pro Pro Glu Lys Pro Phe Asn Ile Ser Cys Trp Ser
        115                 120                 125

Arg Asn Met Lys Asp Leu Thr Cys Arg Trp Thr Pro Gly Ala His Gly
130                 135                 140

Glu Thr Phe Leu His Thr Asn Tyr Ser Leu Lys Tyr Lys Leu Arg Trp
145                 150                 155                 160

Tyr Gly Gln Asp Asn Thr Cys Glu Glu Tyr His Thr Val Gly Pro His
                165                 170                 175

Ser Cys His Ile Pro Lys Asp Leu Ala Leu Phe Thr Pro Tyr Glu Ile
            180                 185                 190

Trp Val Glu Ala Thr Asn Arg Leu Gly Ser Ala Arg Ser Asp Val Leu
        195                 200                 205

Thr Leu Asp Val Leu Asp Val Val Thr Thr Asp Pro Pro Asp Val
210                 215                 220
```

```
His Val Ser Arg Val Gly Gly Leu Glu Asp Gln Leu Ser Val Arg Trp
225                 230                 235                 240

Val Ser Pro Pro Ala Leu Lys Asp Phe Leu Phe Gln Ala Lys Tyr Gln
            245                 250                 255

Ile Arg Tyr Arg Val Glu Asp Ser Val Asp Trp Lys Val Val Asp Asp
                260                 265                 270

Val Ser Asn Gln Thr Ser Cys Arg Leu Ala Gly Leu Lys Pro Gly Thr
            275                 280                 285

Val Tyr Phe Val Gln Val Arg Cys Asn Pro Phe Gly Ile Tyr Gly Ser
            290                 295                 300

Lys Lys Ala Gly Ile Trp Ser Glu Trp Ser His Pro Thr Ala Ala Ser
305                 310                 315                 320

Thr Pro Arg Ser Glu Arg Pro Gly Pro Gly Gly Val Cys Glu Pro
                325                 330                 335

Arg Gly Gly Glu Pro Ser Ser Gly Pro Val Arg Arg Glu Leu Lys Gln
                340                 345                 350

Phe Leu Gly Trp Leu Lys Lys His Ala Tyr Cys Ser Asn Leu Ser Phe
            355                 360                 365

Arg Leu Tyr Asp Gln Trp Arg Ala Trp Met Gln Lys Ser His Lys Thr
            370                 375                 380

Arg Asn Gln Asp Glu Gly Ile Leu Pro Ser Gly Arg Arg Gly Ala Ala
385                 390                 395                 400

Arg Gly Pro Ala Gly
            405

<210> SEQ ID NO 3
<211> LENGTH: 1305
<212> TYPE: DNA
<213> ORGANISM: HUMAN
<220> FEATURE:
<221> NAME/KEY: CDS
<222> LOCATION: (1)..(1302)

<400> SEQUENCE: 3 cgg ccg ccg ccg ttg ctg ccc ctg ctg ctg ctc tgc gtc ctc ggg        48
Arg Pro Pro Pro Leu Leu Pro Leu Leu Leu Leu Cys Val Leu Gly
 1               5                  10                  15 gcg ccg cga gcc gga tca gga gcc cac aca gct gtg atc agt ccc cag    96
Ala Pro Arg Ala Gly Ser Gly Ala His Thr Ala Val Ile Ser Pro Gln
             20                  25                  30 gat ccc acg ctt ctc atc ggc tcc tcc ctg ctg gcc acc tgc tca gtg   144
Asp Pro Thr Leu Leu Ile Gly Ser Ser Leu Leu Ala Thr Cys Ser Val
         35                  40                  45 cac gga gac cca cca gga gcc acc gcc gag ggc ctc tac tgg acc ctc   192
His Gly Asp Pro Pro Gly Ala Thr Ala Glu Gly Leu Tyr Trp Thr Leu
 50                  55                  60 aac ggg cgc cgc ctg ccc cct gag ctc tcc cgt gta ctc aac gcc tcc   240
Asn Gly Arg Arg Leu Pro Pro Glu Leu Ser Arg Val Leu Asn Ala Ser
 65                  70                  75                  80 acc ttg gct ctg gcc ctg gcc aac ctc aat ggg tcc agg cag cgg tcg   288
Thr Leu Ala Leu Ala Leu Ala Asn Leu Asn Gly Ser Arg Gln Arg Ser
                 85                  90                  95 ggg gac aac ctc gtg tgc cac gcc cgt gac ggc agc atc ctg gct ggc   336
Gly Asp Asn Leu Val Cys His Ala Arg Asp Gly Ser Ile Leu Ala Gly
            100                 105                 110 tcc tgc ctc tat gtt ggc ctg ccc cca gag aaa ccc gtc aac atc agc   384
Ser Cys Leu Tyr Val Gly Leu Pro Pro Glu Lys Pro Val Asn Ile Ser
        115                 120                 125
```

-continued

| | | | | | | | | | | | | | | | |
|---|---|---|---|---|---|---|---|---|---|---|---|---|---|---|---|
| tgc | tgg | tcc | aag | aac | atg | aag | gac | ttg | acc | tgc | cgc | tgg | acg | cca | ggg | 432 |
| Cys | Trp | Ser | Lys | Asn | Met | Lys | Asp | Leu | Thr | Cys | Arg | Trp | Thr | Pro | Gly |
| 130 | | | | | 135 | | | | | 140 | | | | | |

| gcc | cac | ggg | gag | acc | ttc | ctc | cac | acc | aac | tac | tcc | ctc | aag | tac | aag | 480 |
| Ala | His | Gly | Glu | Thr | Phe | Leu | His | Thr | Asn | Tyr | Ser | Leu | Lys | Tyr | Lys |
| 145 | | | | | 150 | | | | | 155 | | | | | 160 |

| ctt | agg | tgg | tat | ggc | cag | gac | aac | aca | tgt | gag | gag | tac | cac | aca | gtg | 528 |
| Leu | Arg | Trp | Tyr | Gly | Gln | Asp | Asn | Thr | Cys | Glu | Glu | Tyr | His | Thr | Val |
| | | | | 165 | | | | | 170 | | | | | 175 | |

| ggg | ccc | cac | tcc | tgc | cac | atc | ccc | aag | gac | ctg | gct | ctc | ttt | acg | ccc | 576 |
| Gly | Pro | His | Ser | Cys | His | Ile | Pro | Lys | Asp | Leu | Ala | Leu | Phe | Thr | Pro |
| | | | 180 | | | | | 185 | | | | | 190 | | |

| tat | gag | atc | tgg | gtg | gag | gcc | acc | aac | cgc | ctg | ggc | tct | gcc | cgc | tcc | 624 |
| Tyr | Glu | Ile | Trp | Val | Glu | Ala | Thr | Asn | Arg | Leu | Gly | Ser | Ala | Arg | Ser |
| | | 195 | | | | | 200 | | | | | 205 | | | |

| gat | gta | ctc | acg | ctg | gat | atc | ctg | gat | gtg | ggg | tcc | cac | ctg | ccc | ctc | 672 |
| Asp | Val | Leu | Thr | Leu | Asp | Ile | Leu | Asp | Val | Gly | Ser | His | Leu | Pro | Leu |
| | 210 | | | | | 215 | | | | | 220 | | | | |

| ccc | agc | ccg | gca | act | ccc | ggg | ttg | tcc | ctg | ctg | gtc | aga | ggg | aag | gta | 720 |
| Pro | Ser | Pro | Ala | Thr | Pro | Gly | Leu | Ser | Leu | Leu | Val | Arg | Gly | Lys | Val |
| 225 | | | | | 230 | | | | | 235 | | | | | 240 |

| gtg | acc | acg | gac | ccc | ccg | ccc | gac | gtg | cac | gtg | agc | cgc | gtc | ggg | ggc | 768 |
| Val | Thr | Thr | Asp | Pro | Pro | Pro | Asp | Val | His | Val | Ser | Arg | Val | Gly | Gly |
| | | | | 245 | | | | | 250 | | | | | 255 | |

| ctg | gag | gac | cag | ctg | agc | gtg | cgc | tgg | gtg | tcg | cca | ccc | gcc | ctc | aag | 816 |
| Leu | Glu | Asp | Gln | Leu | Ser | Val | Arg | Trp | Val | Ser | Pro | Pro | Ala | Leu | Lys |
| | | | 260 | | | | | 265 | | | | | 270 | | |

| gat | ttc | ctc | ttt | caa | gcc | aaa | tac | cag | atc | cgc | tac | cga | gtg | gag | gac | 864 |
| Asp | Phe | Leu | Phe | Gln | Ala | Lys | Tyr | Gln | Ile | Arg | Tyr | Arg | Val | Glu | Asp |
| | | 275 | | | | | 280 | | | | | 285 | | | |

| agt | gtg | gac | tgg | aag | gtg | gtg | gac | gat | gtg | agc | aac | cag | acc | tcc | tgc | 912 |
| Ser | Val | Asp | Trp | Lys | Val | Val | Asp | Asp | Val | Ser | Asn | Gln | Thr | Ser | Cys |
| | 290 | | | | | 295 | | | | | 300 | | | | |

| cgc | ctg | gcc | ggc | ctg | aaa | ccc | ggc | acc | gtg | tac | ttc | gtg | caa | gtg | cgc | 960 |
| Arg | Leu | Ala | Gly | Leu | Lys | Pro | Gly | Thr | Val | Tyr | Phe | Val | Gln | Val | Arg |
| 305 | | | | | 310 | | | | | 315 | | | | | 320 |

| tgc | aac | ccc | ttt | ggc | atc | tat | ggc | tcc | aag | aaa | gcc | ggg | atc | tgg | agt | 1008 |
| Cys | Asn | Pro | Phe | Gly | Ile | Tyr | Gly | Ser | Lys | Lys | Ala | Gly | Ile | Trp | Ser |
| | | | | 325 | | | | | 330 | | | | | 335 | |

| gag | tgg | agc | cac | ccc | aca | gcc | gcc | tcc | act | ccc | cgc | agt | gag | cgc | ccg | 1056 |
| Glu | Trp | Ser | His | Pro | Thr | Ala | Ala | Ser | Thr | Pro | Arg | Ser | Glu | Arg | Pro |
| | | | 340 | | | | | 345 | | | | | 350 | | |

| ggc | ccg | ggc | ggc | ggg | gcg | tgc | gaa | ccg | cgg | ggc | gga | gag | ccg | agc | tcg | 1104 |
| Gly | Pro | Gly | Gly | Gly | Ala | Cys | Glu | Pro | Arg | Gly | Gly | Glu | Pro | Ser | Ser |
| | | 355 | | | | | 360 | | | | | 365 | | | |

| ggg | ccg | gtg | cgg | cgc | gag | ctc | aag | cag | ttc | ctg | ggc | tgg | ctc | aag | aag | 1152 |
| Gly | Pro | Val | Arg | Arg | Glu | Leu | Lys | Gln | Phe | Leu | Gly | Trp | Leu | Lys | Lys |
| | 370 | | | | | 375 | | | | | 380 | | | | |

| cac | gcg | tac | tgc | tcc | aac | ctc | agc | ttc | cgc | ctc | tac | gac | cag | tgg | cga | 1200 |
| His | Ala | Tyr | Cys | Ser | Asn | Leu | Ser | Phe | Arg | Leu | Tyr | Asp | Gln | Trp | Arg |
| 385 | | | | | 390 | | | | | 395 | | | | | 400 |

| gcc | tgg | atg | cag | aag | tcg | cac | aag | acc | cgc | aac | cag | cac | agg | acg | agg | 1248 |
| Ala | Trp | Met | Gln | Lys | Ser | His | Lys | Thr | Arg | Asn | Gln | His | Arg | Thr | Arg |
| | | | | 405 | | | | | 410 | | | | | 415 | |

```
gga tcc tgc cct cgg gca gac ggg gca cgg cga gag gtc ctg cca gat    1296
Gly Ser Cys Pro Arg Ala Asp Gly Ala Arg Arg Glu Val Leu Pro Asp
            420                 425                 430 aag ctg tag                                                        1305
Lys Leu
```

<210> SEQ ID NO 4
<211> LENGTH: 434
<212> TYPE: PRT
<213> ORGANISM: HUMAN

<400> SEQUENCE: 4

```
Arg Pro Pro Leu Leu Pro Leu Leu Leu Leu Cys Val Leu Gly
 1               5                  10                  15

Ala Pro Arg Ala Gly Ser Gly Ala His Thr Ala Val Ile Ser Pro Gln
            20                  25                  30

Asp Pro Thr Leu Leu Ile Gly Ser Ser Leu Leu Ala Thr Cys Ser Val
            35                  40                  45

His Gly Asp Pro Pro Gly Ala Thr Ala Glu Gly Leu Tyr Trp Thr Leu
 50                  55                  60

Asn Gly Arg Arg Leu Pro Pro Glu Leu Ser Arg Val Leu Asn Ala Ser
 65                  70                  75                  80

Thr Leu Ala Leu Ala Leu Ala Asn Leu Asn Gly Ser Arg Gln Arg Ser
                 85                  90                  95

Gly Asp Asn Leu Val Cys His Ala Arg Asp Gly Ser Ile Leu Ala Gly
            100                 105                 110

Ser Cys Leu Tyr Val Gly Leu Pro Pro Glu Lys Pro Val Asn Ile Ser
            115                 120                 125

Cys Trp Ser Lys Asn Met Lys Asp Leu Thr Cys Arg Trp Thr Pro Gly
 130                 135                 140

Ala His Gly Glu Thr Phe Leu His Thr Asn Tyr Ser Leu Lys Tyr Lys
 145                 150                 155                 160

Leu Arg Trp Tyr Gly Gln Asp Asn Thr Cys Glu Glu Tyr His Thr Val
                 165                 170                 175

Gly Pro His Ser Cys His Ile Pro Lys Asp Leu Ala Leu Phe Thr Pro
            180                 185                 190

Tyr Glu Ile Trp Val Glu Ala Thr Asn Arg Leu Gly Ser Ala Arg Ser
            195                 200                 205

Asp Val Leu Thr Leu Asp Ile Leu Asp Val Gly Ser His Leu Pro Leu
 210                 215                 220

Pro Ser Pro Ala Thr Pro Gly Leu Ser Leu Leu Val Arg Gly Lys Val
 225                 230                 235                 240

Val Thr Thr Asp Pro Pro Asp Val His Val Ser Arg Val Gly Gly
                 245                 250                 255

Leu Glu Asp Gln Leu Ser Val Arg Trp Val Ser Pro Ala Leu Lys
            260                 265                 270

Asp Phe Leu Phe Gln Ala Lys Tyr Gln Ile Arg Tyr Arg Val Glu Asp
            275                 280                 285

Ser Val Asp Trp Lys Val Val Asp Asp Val Ser Asn Gln Thr Ser Cys
 290                 295                 300

Arg Leu Ala Gly Leu Lys Pro Gly Thr Val Tyr Phe Val Gln Val Arg
 305                 310                 315                 320

Cys Asn Pro Phe Gly Ile Tyr Gly Ser Lys Lys Ala Gly Ile Trp Ser
                 325                 330                 335
```

-continued

```
Glu Trp Ser His Pro Thr Ala Ala Ser Thr Pro Arg Ser Glu Arg Pro
            340                 345                 350

Gly Pro Gly Gly Gly Ala Cys Glu Pro Arg Gly Gly Glu Pro Ser Ser
            355                 360                 365

Gly Pro Val Arg Arg Glu Leu Lys Gln Phe Leu Gly Trp Leu Lys Lys
        370                 375                 380

His Ala Tyr Cys Ser Asn Leu Ser Phe Arg Leu Tyr Asp Gln Trp Arg
385                 390                 395                 400

Ala Trp Met Gln Lys Ser His Lys Thr Arg Asn Gln His Arg Thr Arg
                405                 410                 415

Gly Ser Cys Pro Arg Ala Asp Gly Ala Arg Arg Glu Val Leu Pro Asp
            420                 425                 430

Lys Leu
```